(12) United States Patent
Fukuchi et al.

(10) Patent No.: US 9,364,428 B2
(45) Date of Patent: Jun. 14, 2016

(54) HERB MEDICINE COMPOSITION IN THE FORM OF JELLY

(75) Inventors: Tsunehiro Fukuchi, Higashikagawa (JP); Koji Matsuura, Higashikagawa (JP); Noboru Tatsumi, Saitama (JP); Masatake Dairaku, Saitama (JP); Mitsuo Togashi, Saitama (JP)

(73) Assignee: TEIKOKU SEIYAKU CO., LTD., Kagawa (JP)

( * ) Notice: Subject to any disclaimer, the term of this patent is extended or adjusted under 35 U.S.C. 154(b) by 0 days.

(21) Appl. No.: 10/522,603

(22) PCT Filed: Jul. 28, 2003

(86) PCT No.: PCT/JP03/09529
§ 371 (c)(1),
(2), (4) Date: Jan. 26, 2005

(87) PCT Pub. No.: WO2004/010969
PCT Pub. Date: Feb. 5, 2004

(65) Prior Publication Data
US 2005/0175628 A1    Aug. 11, 2005

(30) Foreign Application Priority Data
Jul. 29, 2002    (JP) ................................ 2002-220191

(51) Int. Cl.
*A61K 9/06* (2006.01)
*A61K 9/00* (2006.01)
*A61K 36/48* (2006.01)
*A61K 47/36* (2006.01)

(52) U.S. Cl.
CPC .............. *A61K 9/0056* (2013.01); *A61K 9/06* (2013.01); *A61K 36/48* (2013.01); *A61K 47/36* (2013.01)

(58) Field of Classification Search
None
See application file for complete search history.

(56) References Cited

U.S. PATENT DOCUMENTS

| | | | | |
|---|---|---|---|---|
| 5,002,934 | A * | 3/1991 | Norton et al. | 514/54 |
| 5,932,235 | A * | 8/1999 | Ninomiya et al. | 424/401 |
| 6,048,564 | A * | 4/2000 | Young et al. | 426/573 |
| 6,063,366 | A * | 5/2000 | Sugai et al. | 424/69 |
| 6,277,395 | B1 * | 8/2001 | Fukui et al. | 424/439 |
| 6,703,063 | B2 * | 3/2004 | Takatsu | 426/575 |
| 2007/0212460 | A1 * | 9/2007 | Inoue et al. | 426/268 |

FOREIGN PATENT DOCUMENTS

| | | | |
|---|---|---|---|
| JP | 54070420 A * | 6/1979 | |
| JP | 63239228 A * | 3/1987 | |
| JP | 3-247699 | 11/1991 | |
| JP | 04-346937 | 12/1992 | |
| JP | 04346937 A * | 12/1992 | |
| JP | 404346937 A * | 12/1992 | |
| JP | 07118161 A * | 5/1995 | |
| JP | 09-012463 | 1/1997 | |
| JP | 09286735 A * | 11/1997 | |
| JP | 11-217329 | 8/1999 | |
| JP | 2001-114696 | 4/2001 | |
| JP | 2001-226293 | 8/2001 | |
| JP | 2002-249437 | 9/2002 | |
| WO | WO 00/24273 | * | 5/2000 |

OTHER PUBLICATIONS http://www.absoluteastronomy.com/topics/Locust_bean_gum.*
Nagasaka et al., Efficacy of kakkon-to, a traditional herb medicine, in herpes simplex virus type 1 infection in mice, 1995, J Med Virol, 46: 28-34.*
English abstract of Japanese Patent Publication B 7-116049 published Dec. 13, 1995.
English abstract of Japanese Patent No. 2508547 published Jun. 19, 1996.
English abstract of Japanese Patent Publication A 9-187233 published Jul. 22, 1997 and A 9-194346 published Jul. 29, 1997.
English abstract of Japanese Patent Publication A 2001-114696 published Apr. 24, 2001.
Supplementary European Search Report issued in the corresponding European Application No. 03 77 1378 on Dec. 9, 2008.
XP-002505098, Database WPI Week 199846, AN 1998-537401, Sep. 8, 1998.
XP-002505099, Database WPI Week 200108, AN 2001-065429, Oct. 10, 2000.
XP-002505100, Database WPI Week 200170, AN 2001-609893, Aug. 21, 2001.
XP-002525101, Database WPI Week 199712, AN 1997-128653, Jan. 14, 1997.

* cited by examiner

*Primary Examiner* — Terry A McKelvey
*Assistant Examiner* — Catheryne Chen
(74) *Attorney, Agent, or Firm* — Wenderoth, Lind & Ponack, L.L.P.

(57) ABSTRACT

A Chinese herbal medical composition in the form of jelly, wherein a Chinese herbal medicine is contained in a base containing at least one substance selected from the group consisting of carrageenan, carob bean gum and xanthan gum and not containing phosphate buffer. The Chinese herbal medical composition hardly causes syneresis, is superior in the preservative stability, is broadly applicable to a Chinese herbal medicine and is orally taken without taking care of the bitter of a Chinese herbal medicine.

19 Claims, 1 Drawing Sheet

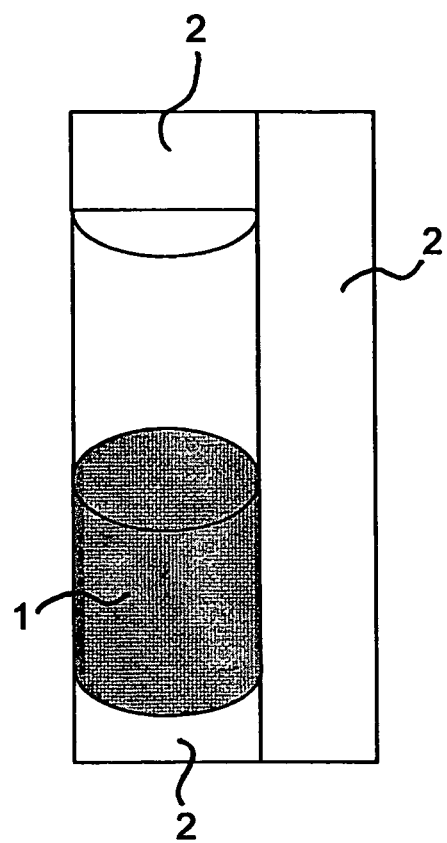

HERB MEDICINE COMPOSITION IN THE FORM OF JELLY

TECHNICAL FIELD OF THE INVENTION

The present invention relates to a Chinese herbal medical composition in the form of jelly, which hardly causes syneresis, is superior in the preservative stability, is broadly applicable to Chinese herbal medicine (漢方薬), and can be orally taken without taking care of the bitter taste, etc., of the Chinese herbal medicine.

BACKGROUND OF THE INVENTION

The traditional Chinese herbal medicines are in the forms of liquids prepared by decocting crude drugs (生薬), powders prepared by powdering crude drugs or pills made of crude drugs and honey. Therefore, traditional Chinese herbal medicines have the disadvantages of being inconvenient due to the time required to decoct crude drugs, and due to having to prepare it according to necessity. Furthermore, it is painful or difficult for a patient to take the decoction or the powdered crude drug, due to the bitter taste or smell, which are peculiar to Chinese herbal medicines. Today, in order to solve such problems, Chinese herbal medical preparations, such as extracts from a Chinese herbal medicine, powders, granules, tablets, liquids, etc., are prepared starting from the powdered crude drugs. These preparations solve the inconveniences due to taking time to decoct crude drugs, and having to prepare it according to necessity. These preparations are also superior in preservative stability.

However, a patient must take several grams of preparation in the form of powders, granules or tablets, and this is a burden for the patient. Further, the powders and the granules can cause problems such as choking, resulting in a sandy feeling in a mouth, or getting between false teeth when they are taken. The tablets can be too large for a patient to take. The taste and smell peculiar to a Chinese herbal medicine is improved by tabletting it. However, there are still disadvantages in that a Chinese herbal medicine is strongly tasted, is unpleasant, and is difficult to take when the contents in the tablets dissolve, or the tablets disintegrate in a mouth while taking them.

On the other hand, the liquids are more easily taken compared to the powders, the granules and the tablets. However, the liquids have troubles in that the bitter taste and smell peculiar to a Chinese herbal medicine becomes strong, because the liquid is broadly spread in a mouth. Therefore, it is painful and difficult to take a liquid formulation. Furthermore, it is inconvenient to carry as it is packed in a glass-bottle. In order to solve such problems with a Chinese herbal medical preparation, it is considered to make a Chinese herbal medicine in the form of jelly.

As a jelly preparation containing a Chinese herbal medicine, there is known a jelly preparation made of a Chinese herbal medicine and gelatin (Japanese patent publication B 7-116049). As gelatin is a gelling agent which is physicochemically unstable, the preparation lacks preservative stability and must be stored in a cold place. Therefore, it does not stand for the test for medicines (the long term-preservation test at 25° C. under 60% RH for 3 years, or the accelerated preservation test at 40° C. under 75% RH for 6 months, etc.). In addition, gelatin is easily dissolved in a mouth and therefore, the preparation easily gives the bitter taste and is difficult to take when a Chinese herbal medicine having the strong bitter taste is contained.

In addition, it is considered that a jelly preparation containing Chinese herbal medicine is prepared using sodium alginate or agar. As a jelly preparation containing a Chinese herbal medicine using sodium alginate, a jelly preparation containing Sho-saiko-to is known (小柴胡湯) (Japanese patent No. 2508547). The bitter taste peculiar to a Chinese herbal medicine can be masked by adding alginic acid. However, as jelly containing alginic acid causes much syneresis, heterogeneity of the drug occurs and the drug remains in the packed vessel when taking it. The appearance is also bad. Therefore, the preparation is not preferable as a medicine.

In regard to a jelly preparation prepared using agar, the preparation causes much syneresis, similar to the preparation containing alginic acid. Further, the preparation easily disintegrates in a mouth, easily gives the bitter taste and does not give a good feeling when taking it.

As other jelly preparations, a jelly composition (Japanese patent publication A 9-187233 and Japanese patent publication A 9-194346) and a Chinese herbal medical composition in the form of jelly (Japanese patent publication A 2001-114696) are known, but it is very difficult to prepare jelly preparations containing a Chinese herbal medicine which guarantees the preservative stability on a medical level.

The following reasons are considered as causes which make it difficult to make a Chinese herbal medicine in the form of jelly.

The preparation contains as a starting material, a natural product which consists of a variety of ingredients, and many of these ingredients are structurally unknown. In addition, there are many forms of starting materials, such as crude drugs, liquid extract, condensed extract, dry extract, soft extract, fluid extract, etc., and the dosages on them vary.

As there is such a background peculiar to a Chinese herbal medicine, when a Chinese herbal medicine is formed into a jelly preparation, according to the kind or amount of the contained Chinese herbal medicine, there are possibilities to produce the preparation wherein its appearance can not be maintained due to syneresis and the stability of the active ingredients can not be maintained. Therefore, a Chinese herbal medical composition in the form of jelly which is broadly applicable has been desired.

BRIEF SUMMARY OF THE INVENTION

The present invention was completed based on the above viewpoint and the goal is to provide a Chinese herbal medical composition in the form of jelly, which hardly causes syneresis, is superior in the preservative stability, is broadly applicable to a Chinese herbal medicine, and is orally taken without taking care of the bitter, etc., of a Chinese herbal medicine.

The present inventors have extensively studied to solve the above problems, and have found that by using at least one substance selected from the group consisting of carrageenan, carob bean gum and xanthan gum as a base (not containing phosphate buffer) of the jelly preparation containing a Chinese herbal medicine, a Chinese herbal medical composition in the form of jelly, which hardly causes syneresis, is superior in the preservative stability, is broadly applicable to a Chinese herbal medicine, and is orally taken without taking care of the bitter, etc., of a Chinese herbal medicine is obtainable. Thus, the present invention was completed.

BRIEF DESCRIPTION OF THE DRAWINGS

FIG. 1 shows a stick-like packed vessel which is sealed on three parts.

EXPLANATION OF SIGNS

1: A Chinese herbal medical composition in the form of jelly
2: Sealed parts

DETAILED DESCRIPTION OF THE INVENTION

Carrageenan used in the Chinese herbal medical composition in the form of jelly of the present invention is not limited as long as it is usually used for a jelly composition. For example, there are κ (kappa) type, ι (iota) type and λ (lambda) type, with respect to carrageenan. Any type is usable, but preferably a combination of ι type carrageenan and either κ type carrageenan or λ type carrageenan, or a combination of these three type carageenans, or ι type carrageenan solely is usable. When a combination of ι type carrageenan and either κ type carrageenan or λ type carrageenan, or a combination of these three type carageenans is used, ι type carrageenan is usually used in the amount of more than 50 w/w % per total carageenan weight, preferably more than 70 w/w %, and more preferably more than 95 w/w %.

The amount of carageenan contained in the Chinese herbal medical composition in the form of jelly of the present invention is preferably 0.01~10.0 w/w % per total amount of the composition, more preferably 0.05~5.0 w/w %, and further more preferably 0.08~2.0 w/w %. When the amount of carrageenan is beyond the above range, the preparation becomes too viscous to prepare it, and when the amount is below the above range, the jelly formation becomes difficult and the desired composition is not obtainable.

Carob bean gum used in the Chinese herbal medical composition in the form of jelly of the present invention is not limited as long as it is usually used for a jelly composition.

The amount of carob bean gum contained in the Chinese herbal medical composition in the form of jelly of the present invention is preferably 0.01~10.0 w/w % per total amount of the composition, more preferably 0.05~5.0 w/w %, and further more preferably 0.1~2.0 w/w %. When the amount of carob bean gum is beyond the above range, the preparation becomes too viscous to prepare it, and when the amount is below the above range, the jelly formation becomes difficult and the desired composition is not obtainable.

Xanthan gum used in the Chinese herbal medical composition in the form of jelly of the present invention is not limited as long as it is usually used for a jelly composition.

The amount of xanthan gum contained in the Chinese herbal medical composition in the form of jelly of the present invention is preferably 0.01~10.0 w/w % per total amount of the composition, more preferably 0.05~5.0 w/w %, and further more preferably 0.08~2.0 w/w %. When the amount of xanthan gum is beyond the above range, the preparation becomes too viscous to prepare it, and when the amount is below the above range, the jelly formation becomes difficult and the desired composition is not obtainable.

The amount of a Chinese herbal medicine contained in the Chinese herbal medical composition in the form of jelly of the present invention is preferably less than 60 w/w % per total amount of the composition, more preferably less than 50 w/w %, and further more preferably less than 30 w/w %. When the amount of the Chinese herbal medicine is beyond the above range, there is a possibility that the preparation becomes too viscous to prepare it and the jelly formation becomes difficult due to it being rice cake or jam-like.

A dispersion medium in order to disperse a base which is used for a Chinese herbal medical composition in the form of jelly of the present invention includes a liquid which is usually used as a dispersion medium of a jelly composition, for example water or a mixture of water and a polyalcohol. Examples of the polyalcohol are glycerin, propylene glycol, etc. The amount of the dispersion medium of a Chinese herbal medical composition in the form of jelly of the present invention is, preferably 30~90 w/w % per total composition, more preferably 30~85 w/w %, and further more preferably 40~80 w/w %.

The Chinese herbal medical composition in the form of jelly of the present invention may, if necessary, contain various known ingredients which are acceptable as medical additives and are orally administrable, such as stabilizing agents, correctives, sweetening agents, emulsifying agents, dispersion agents, preservatives, flavors, coloring agents, etc.

The stabilizing agent, if desired, contained in the Chinese herbal medical composition in the form of jelly of the present invention includes ascorbic acid, disodium edetate, tocopherol, etc. The corrective includes citric acid, malic acid, lactic acid, succinic acid, tartaric acid, ascorbic acid, a citrate, a malate, a lactate, a succinate, a tartarate, etc. The sweetening agent includes glucose, fructose, saccharin sodium, sucrose, D-sorbitol, D-mannitol, hydrogenated maltose starch syrup, etc. The emulsifying agent includes polyoxyethylene sorbitan monooleate, sodium lauryl sulfate, etc. The dispersion agent includes an aqueous high molecular weight compound, such as carboxymethylcellulose, sodium alginate, hydroxypropylcellulose, hydroxyethylcellulose, etc. The preservative includes methyl parahydroxybenzoate (methylparaben), ethyl parahydroxybenzoate (ethylparaben), etc. The flavor includes ones such as menthols, fruit juices, or essential oils. The coloring agent includes caramel, etc.

The raw material contained in the Chinese herbal medical composition in the form of jelly of the present invention is not limited as long as it is an ordinary Chinese herbal medicine. For example, Kakkon-to (葛根湯) Sho-seiryu-to (小青竜湯), Sho-saiko-to (小柴胡湯), Hachimi-jio-gan (八味地黄丸), Hochu-ekki-to (補中益気湯), Sho-kenchu-to (小建中湯), Shofu-san (消風散), Seijo-bofu-to (清上防風湯), Bofu-tsusho-san (防風通聖散), Gorei-san (五苓散), Boi-ogi-to (防已黄耆湯), Otsuji-to (乙字湯), Toki-shakuyaku-san (当帰芍薬散), Keishi-bukuryo-gan (桂枝茯苓丸), Anchu-san (安中散), Heii-san (平胃散), etc., are illustrated. Further, a variety of Chinese herbal medicines are usable as well. The raw material is not only limited to Chinese herbal medicines, but also the raw material made of natural plants is usable in the Chinese herbal medical composition in the form of jelly of the present invention. The raw material selected from Chinese herbal medicines and natural plants is usable in combination with other active substances in the Chinese herbal medical composition in the form of jelly of the present invention. For example, a combination of a cold medicine, an antitussive, an expectorant, and/or a medicine for stomach with a western medicine is usable.

The raw material is not limited as long as it is a usual Chinese herbal medicine or natural plant. For example, a crude drug, liquid extract, condensed extract, dry extract, soft extract, fluid extract, etc., are illustrated. The amount of the raw material may be contained in order that the suitable dosage is obtained when a Chinese herbal medical composition in the form of jelly is taken in the defined amount.

The method for preparing the Chinese herbal medical composition in the form of jelly of the present invention can be the same manner as in a usually known method for jelly preparations. For example, the suitable amount of warmed water as a dispersion medium is added to a base and a raw material and if necessary, a desired substance, and the mixture is stirred to be dispersed, dissolved or suspended, or otherwise the suitable amount of water or cold water as a dispersion medium is added to a base and a raw material and if necessary, a desired substance at room temperature. The mixture is stirred under warming to be dispersed, dissolved or suspended and the resulting drug is cooled to prepare the Chinese herbal medical composition in the form of jelly. Further, when an ingredient which is not preferable to be exposed to high temperature is contained among a base and a raw material and if necessary, a desired substance, it may be added after the dispersion, the solution or the suspension prepared above is adjusted to moderate temperature to prepare the Chinese herbal medical composition in the form of jelly. Otherwise an ingredient which is not preferable to be exposed to high temperature may be added thereto just before cooling to prepare the Chinese herbal medical composition in the form of jelly.

The packed vessel for the Chinese herbal medical composition in the form of jelly of the present invention is not specifically limited, but a stick-like vessel or a bag-like vessel is preferable in respect of carrying and taking it.

EXAMPLES

The present invention is explained by following examples and is not limited by these examples.

Examples 1~4 and Comparative Examples 1~6

In regard to Examples 1~4 and Comparative examples 1, 5 and 6, the ingredients shown in Tables 1-1 and 1-2 were weighed and each ingredient was dissolved under heating at 80° C. The resulting solution was poured into a stick-like vessel sealed at three parts and cooled to prepare a Chinese herbal medical composition.

In regard to Comparative examples 2~4, after sodium alginate was homogenously dissolved in water, it was warmed at 50~60° C., and thereto were added aqueous dry extract of Kakkon-to (葛根湯). After the mixture was homogeneously dissolved for about 5 minutes, other residual ingredients were added thereto and stirred homogeneously. The mixture was poured into a stick-like vessel sealed at three parts and was cooled to prepare a Chinese herbal medical composition.

The preparation of Example 1 resulted in a good Chinese herbal medical composition in the form of jelly, but the preparation of Comparative example 1 became like a rice cake without forming a jelly. The preparations of Examples 2~4 and Comparative example 5 resulted in Chinese herbal medical compositions in the form of jelly, but the preparations of Comparative examples 2~4 containing sodium alginate did not form jelly. The preparation of Comparative example 6 containing gelatin resulted in a Chinese herbal medical composition in the form of jelly in a refrigerator, but the preparation was a semi-solid at room temperature.

Examples 5~7

The ingredients shown in Table 2 were weighed and each ingredient was dissolved under heating at 80° C. The resulting solution was poured into a stick-like vessel sealed at three parts and was cooled to prepare a Chinese herbal medical composition in the form of jelly.

Examples 8~10 and Comparative Examples 7~9

In regard to Examples 8~10 and Comparative examples 8 and 9, the ingredients shown in Table 3 were weighed and each ingredient was dissolved under heating at 80° C. The resulting solution was poured into a stick-like vessel sealed at three parts and was cooled to prepare a Chinese herbal medical composition in the form of jelly.

In regard to Comparative example 7, after sodium alginate was homogenously dissolved in water, it was warmed at 50~60° C., and thereto were added aqueous dry extract of Seijo-bofu-to (清上防風湯). After the mixture was homogeneously dissolved for about 5 minutes, other residual ingredients were added thereto and stirred homogeneously. The mixture was poured into a stick-like vessel sealed at three parts and was cooled to prepare a Chinese herbal medical composition in the form of jelly.

The preparations of Examples 8~10 resulted in good Chinese herbal medical compositions in the form of jelly. The preparations of Comparative example 7 and Comparative example 8 containing sodium alginate and agar, respectively resulted in a Chinese herbal medical composition in the form of jelly. The preparation of Comparative example 9 containing gelatin resulted in a Chinese herbal medical composition in the form of jelly in a refrigerator, but the preparation was a semi-solid at room temperature. The preparation of Comparative example 9 was dissolved in a mouth and gave the bitter taste when it was taken, and did not give good feeling (see Table 7). The preparation did not serve as a medicine.

Measurement of the Amount of Syneresis and the Strength of Jelly

According to the method below, the Chinese herbal medical compositions in the form of jelly obtained were stored at 40° C. under 75% RH and at 25° C. under 60% RH, respectively. The amount of syneresis and the strength of jelly were measured on each sample and their appearances were observed.

The Method for Measuring the Amount of Syneresis

The method was carried out by standing on end a stick-like packed vessel sealed at three parts into which a Chinese herbal medical composition in the form of jelly was poured (FIG. 1). The ratio of the weight of syneresis remained in the air portion per total amount was calculated.

The Method for Measuring the Strength on Jelly

The method was carried out by taking out a Chinese herbal medical composition in the form of jelly (sample) from a stick-like packed vessel sealed at three parts (see FIG. 1) after it was stored at 25° C. for 24 hours, and the sample was measured at 25° C. using a tool below.

Measuring tool: Rheometer CR-200D (prepared by San Kagaku)

Measuring conditions: Pressed speed, 30 mm/min

Pressure-sensitive axis: Cross section 5×40 mm×height 15 mm (Stainless)

Results

The results obtained on syneresis of the preparations in the form of jelly of Examples 2~4 and Comparative example 5 were shown in Table 4-1. The preparations of Examples 2~4 were stored both at 40° C. under 75% RH and at 25° C. under 60% RH, and they hardly showed syneresis and their appearances were good. On the other hand, the preparation of Comparative example 5 containing agar showed much syneresis both at 40° C. under 75% RH and at 25° C. under 60% RH. Its appearance was bad and did not serve as a medicine.

The results obtained on the jelly strength on the preparations in the form of jelly of Examples 2~4 and the preparation of Comparative example 5 were shown in Table 4-2. Changes on the jelly strength on the preparations of Examples 2~4 were not observed under the preservation both at 40° C. under 75% RH and 25° C. under 60% RH. On the contrary, rapid increase of the jelly strength was observed on the preparation Comparative example 5 containing agar under the preservation both at 40° C. under 75% RH and at 25° C. under 60% RH in one month.

The preparations of Examples 5~7 resulted in good Chinese herbal medical compositions in the form of jelly, hardly showed syneresis under the preservation conditions both at 0° C. under 75% RH and at 25° C. under 60% RH (see Table 5-1), their appearances were good and changes of the jelly strength on them were not observed (see Table 5-2).

The preparations of Examples 8~10 resulted in good Chinese herbal medical compositions in the form of jelly, hardly showed syneresis under the preservation conditions both at 0° C. under 75% RH and at 25° C. under 60% RH (see Table 6-1). Their appearances were good and changes of the jelly strength on them were not observed (see Table 6-2).

On the contrary the preparations in the form of jelly of Comparative examples 7 and 8 showed much syneresis under the preservation conditions both at 0° C. under 75% RH and at 25° C. under 60% RH (see Table 6-1). Their appearances were bad and the jelly strength on them was greatly changed in one month and they could serve as a medicine (see Table 6-2).

As mentioned above, it was ascertained that the Chinese herbal medical composition in the form of jelly of the present invention hardly shows syneresis for a long time and is superior in the preservative stability compared to a jelly preparation containing either gelatin or sodium alginate as a base.

When sodium alginate is used as a base, the Chinese herbal medical composition in the form of jelly is obtained or not obtained depending on the raw material. On the contrast, according to the present invention the good Chinese herbal medical composition in the form of jelly can be obtained regardless of the raw material.

Masking Effect on Bitter Taste

By using Chinese herbal medical compositions in the form of jelly and a semi-solid preparation containing gelatin (Comparative example 9), which had the ingredients shown in Table 3, the organoleptic test was carried out. The panel tests were carried out by using 10 persons (5 males and 5 females) and the evaluation were shown as follows: ++: too bitter to take one, +: bitter, ±: slightly bitter, −: scarcely bitter, −−: no bitter A preparation which was prepared by dissolving aqueous dry extract of Seijo-bofu-to ( 清上防風湯 ) 7 g in water (100 g) was used as a control.

As shown in Table 7, in regard to the Control and the preparations of Comparative examples 8 and 9, almost all persons answered with "too bitter to take them" (Control and Comparative example 9: 10/10, Comparative example 8: 8/10). On the contrast, in regard to the preparation of Example 10, persons who answered with "too bitter to take it" and "bitter" were 3/10 and 7/10, respectively and these preparations showed better result comparing with the preparations of Control and Comparative examples 8 and 9.

The preparation of Comparative example 7 gave the almost same result as the preparation of Example 10, and persons who answered with "too bitter to take it" and "bitter" were 1/10 and 9/10, respectively. The preparation of Comparative example 7 like the preparation of Example 10 showed a better result than the aqueous solution (control), jelly preparations containing agar and gelatin, respectively (Comparative example 8 and 9). Although it is known that the bitter taste is masked by adding sodium alginate to a bitter taste substance, it seems not to exhibit any masking effect as the extract was much.

In regard to the preparation of Example 9, persons who answered with "slightly bitter" were 7/10 and there was none who answered with "too bitter to take it". In regard to the preparation of Example 8, persons who answered with "slightly bitter" were 8/10 and there was none who answered with "too bitter to take it" or "bitter".

As mentioned above, it was ascertained that a Chinese herbal medical composition in the form of jelly wherein the bitter taste of a Chinese herbal medicine effectively masks was obtainable. Especially by solely using ι carrageenan, it was confirmed that the bitter taste of a Chinese herbal medicine which was contained in the high concentration was excellently masked. Furthermore, by adding a sweetening agent to the Chinese herbal medical composition in the form of jelly prepared by the present invention, it became possible to take it almost without taking care of the bitter taste of a Chinese herbal medicine.

TABLE 1-1

| | Amount (weight %) | | | |
|---|---|---|---|---|
| Ingredient | Ex. 1 | Ex. 2 | Ex. 3 | Ex. 4 |
| Aqueous dry extract of Kakkon-to (葛根湯) | 30 | 15 | 15 | 15 |
| ι Carrageenan | 0.5 | 1 | 1 | — |
| κ Carrageenan | — | — | 0.05 | 1 |
| Carob bean gum | 0.1 | 0.25 | 0.25 | 0.25 |
| Xanthan gum | 0.2 | 0.45 | 0.45 | 0.45 |
| Sodium alginate | — | — | — | — |
| Calcium monohydrogen phosphate | — | — | — | — |
| Glucono-δ-lactone | — | — | — | — |
| Agar | — | — | — | — |
| Gelatin | — | — | — | — |
| Powdered hydrogenated maltose starch syrup | — | 6 | 6 | 6 |
| D-Sorbitol | — | 6 | 6 | 6 |
| Glycerin | — | 6 | 6 | 6 |
| Propylene glycol | — | 1 | 1 | 1 |
| Propyl parahydroxybenzoate | 0.02 | 0.02 | 0.02 | 0.02 |
| Purified water | 69.18 | 64.28 | 64.23 | 64.28 |
| Total | 100 | 100 | 100 | 100 |

TABLE 1-2

| | Amount (weight %) | | | | | |
|---|---|---|---|---|---|---|
| Ingredient | Comp. ex. 1* | Comp. ex. 2* | Comp. ex. 3* | Comp. ex. 4* | Comp. ex. 5 | Comp. ex. 6* |
| Aqueous dry extract of Kakkon-to (葛根湯) | 65 | 5 | 15 | 15 | 15 | 15 |
| ι Carrageenan | 0.5 | — | — | — | — | — |
| κ Carrageenan | — | — | — | — | — | — |
| Carob bean gum | 0.1 | — | — | — | — | — |
| Xanthan gum | 0.2 | — | — | — | — | — |
| Sodium alginate | — | 0.8 | 0.8 | 2 | — | — |
| Calcium monohydrogen phosphate | — | 0.2 | 0.2 | 0.5 | — | — |
| Glucono-δ-lactone | — | 2.2 | 2.2 | — | — | — |

TABLE 1-2-continued

| Ingredient | Comp. ex. 1* | Comp. ex. 2* | Comp. ex. 3* | Comp. ex. 4* | Comp. ex. 5 | Comp. ex. 6* |
|---|---|---|---|---|---|---|
| | Amount (weight %) | | | | | |
| Agar | — | — | — | — | 3 | — |
| Gelatin | — | — | — | — | — | 7.5 |
| Powdered hydrogenated maltose starch syrup | — | — | — | — | — | — |
| D-Sorbitol | — | — | — | — | — | — |
| Glycerin | — | — | — | — | — | — |
| Propylene glycol | — | — | — | — | — | — |
| Propyl parahydroxy-benzoate | 0.02 | 0.02 | 0.02 | 0.02 | 0.02 | 0.02 |
| Purified water | 34.18 | 91.78 | 81.78 | 82.48 | 81.98 | 77.48 |
| Total | 100 | 100 | 100 | 100 | 100 | 100 |

*not solidified

TABLE 2

| Ingredient | Ex. 5 | Ex. 6 | Ex. 7 |
|---|---|---|---|
| | Amount (weight %) | | |
| Soft extract of Hachimi-jio-gan (八味地黄丸) | 14 | — | — |
| Keishi-bukuryo-gan (桂枝茯苓丸) (crude drug) | — | 14 | 14 |
| ι Carrageenan | 1 | 1 | 1 |
| κ Carrageenan | — | — | 0.1 |
| Carob bean gum | 0.2 | 0.25 | 0.25 |
| Xanthan gum | 0.4 | 0.45 | 0.45 |
| Powdered hydrogenated maltose starch syrup | 6 | 6 | 6 |
| D-Sorbitol | 6 | 6 | 6 |
| Glycerin | 6 | 6 | 6 |
| Propylene glycol | 1 | 1 | 1 |
| Propyl parahydroxybenzoate | 0.02 | 0.02 | 0.02 |
| Purified water | 65.38 | 65.28 | 65.18 |
| Total | 100 | 100 | 100 |

TABLE 3

| Ingredient | Ex. 8 | Ex. 9 | Ex. 10 | Comp. ex. 7 | Comp. ex. 8 | Comp. ex. 9* | Control |
|---|---|---|---|---|---|---|---|
| | Amount (weight %) | | | | | | |
| Aqueous dry extract of Seijo-bofu-to (滑上防風湯) | 14 | 14 | 14 | 14 | 14 | 7 | 7 |
| ι Carrageenan | 1 | 1 | — | — | — | — | — |
| κ Carrageenan | — | — | 1 | — | — | — | — |
| Carob bean gum | 0.2 | 0.2 | 0.2 | — | — | — | — |
| Xanthan gum | 0.4 | 0.4 | 0.4 | — | — | — | — |
| Sodium alginate | — | — | — | 2 | — | — | — |
| Calcium monohydrogen phosphate | — | — | — | 0.5 | — | — | — |
| Agar | — | — | — | — | 3 | — | — |
| Gelatin | — | — | — | — | — | 7.5 | — |
| Powdered hydrogenated maltose starch syrup | 6 | — | — | — | — | — | — |
| D-Sorbitol | 6 | — | — | — | — | — | — |
| Glycerin | 6 | — | — | — | — | — | — |
| Propylene glycol | 1 | — | — | — | — | — | — |
| Propyl parahydroxybenzoate | 0.02 | 0.02 | 0.02 | 0.02 | 0.02 | 0.02 | 0.02 |
| Purified water | 65.38 | 84.38 | 84.38 | 83.48 | 82.98 | 85.48 | 92.98 |
| Total | 100 | 100 | 100 | 100 | 100 | 100 | 100 |

*not solidified

TABLE 4-1

| Amount of syneresis (weight %) | Example 2 | Example 3 | Example 4 | Example 5 |
|---|---|---|---|---|
| | 40° C. 75% RH | | | |
| After 2 days | — | — | — | — |
| After one month | 0.2% | 0.4% | 3.3% | 8.2% |
| After 3 months | 0.3% | 1.5% | 4.0% | — |
| After 6 months | 0.8% | 1.9% | 4.4% | — |
| | 25° C. 60% RH | | | |
| After 2 days | no | no | 2.3% | 3.0% |
| After one month | 0.4% | 0.6% | 5.0% | 9.2% |
| After 3 months | 1.2% | 2.0% | 4.8% | — |
| After 6 months | 1.0% | 2.3% | 5.4% | — |

TABLE 4-2

| Strength | Example 2 | Example 3 | Example 4 | Comp. ex. 5 |
|---|---|---|---|---|
| | 40° C. 75% RH | | | |
| Before starting preservation | 293 g | 300 g | 90 g | 143 g |
| After one month | 290 g | 314 g | 88 g | 191 g |
| After 3 months | 302 g | 322 g | 84 g | — |
| After 6 months | 297 g | 323 g | 86 g | — |
| | 25° C. 60% RH | | | |
| Before starting preservation | 293 g | 300 g | 90 g | 143 g |
| After one month | 285 g | 304 g | 87 g | 180 g |
| After 3 months | 297 g | 308 g | 88 g | — |
| After 6 months | 293 g | 322 g | 84 g | — |

TABLE 5-1

| Amount of syneresis | 40° C. 75% RH | | | 25° C. 60% RH | | |
|---|---|---|---|---|---|---|
| (weight %) | Ex. 5 | Ex. 6 | Ex. 7 | Ex. 5 | Ex. 6 | Ex. 7 |
| After 2 days | no | no | no | no | no | no |
| After one month | no | no | no | 0.3% | no | no |
| After 3 months | 0.3% | no | no | 0.7% | no | no |
| After 6 months | 0.5% | no | no | 1.1% | no | no |

TABLE 5-2

| | 40° C. 75% RH | | | 25° C. 60% RH | | |
|---|---|---|---|---|---|---|
| Strength | Ex. 5 | Ex. 6 | Ex. 7 | Ex. 5 | Ex. 6 | Ex. 7 |
| Before starting preservation | 163 g | 158 g | 160 g | 163 g | 158 g | 167 g |
| After one month | 189 g | 155 g | 161 g | 169 g | 158 g | 165 g |
| After 3 months | 182 g | 157 g | 164 g | 181 g | 160 g | 160 g |
| After 6 months | 180 g | 164 g | 166 g | 178 g | 159 g | 163 g |

TABLE 6-1

| Amount of syneresis (weight %) | Ex. 8 | Ex. 9 | Ex. 10 | Comp. ex. 7 | Comp. ex. 8 |
|---|---|---|---|---|---|
| 40° C. 75% RH | | | | | |
| After 2 days | — | — | — | — | — |
| After one month | 0.2% | 0.2% | 4.2% | 9.0% | 10.0% |
| After 3 months | 0.5% | 0.4% | 5.2% | — | — |
| After 6 months | 0.8% | 0.5% | 5.0% | — | — |
| 25° C. 60% RH | | | | | |
| After 2 days | 0.2% | 0.2% | 3.3% | 0.9% | 4.0% |
| After one month | 1.1% | 1.2% | 4.4% | 8.4% | 9.7% |
| After 3 months | 1.0% | 1.3% | 5.1% | — | — |
| After 6 months | 1.2% | 1.4% | 5.2% | — | — |

TABLE 6-2

| Strength | Ex. 8 | Ex. 9 | Ex. 10 | Comp. ex. 7 | Comp. ex. 8 |
|---|---|---|---|---|---|
| 40° C. 75% RH | | | | | |
| Before starting preservation | 276 g | 109 g | 103 g | 105 g | 68 g |
| After one month | 292 g | 122 g | 100 g | 69 g | 153 g |
| After 3 months | 286 g | 118 g | 111 g | — | — |
| After 6 months | — | 296 g | 114 g | — | — |
| 25° C. 60% RH | | | | | |
| Before starting preservation | 276 g | 109 g | 103 g | 105 g | 68 g |
| After one month | 287 g | 111 g | 114 g | 64 g | 139 g |
| After 3 months | 284 g | 110 g | 116 g | — | — |
| After 6 months | 282 g | 118 g | 118 g | — | — |

TABLE 7

| Olganoleptic test | Evaluation (Unit: person) | | | | |
|---|---|---|---|---|---|
| | ++ | + | ± | − | −− |
| Ex. 8 | 0 | 0 | 2 | 8 | 0 |
| Ex. 9 | 0 | 3 | 7 | 0 | 0 |
| Ex. 10 | 3 | 7 | 0 | 0 | 0 |
| Comp. ex. 7 | 1 | 9 | 0 | 0 | 0 |
| Comp. ex. 8 | 8 | 2 | 0 | 0 | 0 |

TABLE 7-continued

| Olganoleptic test | Evaluation (Unit: person) | | | | |
|---|---|---|---|---|---|
| | ++ | + | ± | − | −− |
| Comp. ex. 9 | 10 | 0 | 0 | 0 | 0 |
| Control | 10 | 0 | 0 | 0 | 0 |

++: too bitter to take one
+: bitter
±: slightly bitter
−: scarcely bitter
−−: no bitter

INDUSTRIAL APPLICABILITY

In the present invention, by using at least one substance selected from the group consisting of carrageenan, carob bean gum and xanthan gum as a base (not containing phosphate buffer) of the jelly preparation containing a Chinese herbal medicine, a Chinese herbal medical composition in the form of jelly, which hardly causes syneresis, is superior in the preservative stability, is broadly applicable to a Chinese herbal medicine, and is orally taken without taking care of bitter, etc., of a Chinese herbal medicine is obtainable. Furthermore, even when the Chinese herbal medical composition in the form of jelly of the present invention can stand for the test for medicines, for example the long term-preservation test at 25° C. under 60% RH for 3 years, and the accelerated preservation test at 40° C. under 75% RH for 6 months and is guaranteed in the preservative stability.

The invention claimed is:

1. A Chinese herbal medical composition in the form of jelly, consisting of a Chinese herbal medicine in a base,
   wherein the Chinese herbal medicine is selected from the group consisting of Kakkon-to and Sho-saiko-to, and is present in an amount from 14 w/w % to less than 60 w/w % per total amount of the composition,
   wherein the base consists of 0.01 to 10.0 w/w % carrageenan, 0.01 to 10.0 w/w % carob bean gum, 0.01 to 10.0 w/w % xanthan gum, per total amount of the composition, and at least one pharmaceutically acceptable additive selected from the group consisting of a stabilizing agent, a corrective agent, an emulsifying agent, a dispersion agent, a sweetening agent, a flavoring agent, a coloring agent, and a preservative,
   wherein the carrageenan is iota carrageenan alone, and
   wherein the base does not include a phosphate buffer or agar.

2. The Chinese herbal medical composition according to claim 1,
   wherein the Chinese herbal medicine is present in an amount less than 30 w/w % per total amount of the composition, and
   wherein the base consists of 0.08 to 2.0 w/w % carrageenan, 0.1 to 2.0 w/w % carob bean gum, and 0.08 to 2.0 w/w % xanthan gum, per total amount of the composition, and at least one pharmaceutically acceptable additive selected from the group consisting of a stabilizing agent, a corrective agent, an emulsifying agent, a dispersion agent, a sweetening agent, a flavoring agent, a coloring agent, and a preservative.

3. The Chinese herbal medical composition according to claim 1, wherein the amount of the Chinese herbal medicine is 14 to 30 w/w % per total amount of the composition.

4. A process for preparing the Chinese herbal medical composition according to claim 1, comprising:

mixing the Kakkon-to or Sho-saiko-to with the carrageenan, the carob bean gum, the xanthan gum, and the at least one pharmaceutically acceptable additive, and then adding warm water to the mixture or adding water to the mixture and further warming it, wherein the resulting composition is stable.

5. The Chinese herbal medical composition according to claim 1, wherein the Chinese herbal medicine is present in an amount less than 50 w/w % per total amount of the composition, and wherein the base consists of 0.05 to 5.0 w/w % carrageenan, 0.05 to 5.0 w/w % carob bean gum, and 0.05 to 5.0 w/w % xanthan gum, per total amount of the composition, and at least one pharmaceutically acceptable additive selected from the group consisting of a stabilizing agent, a corrective agent, an emulsifying agent, a dispersion agent, a sweetening agent, a flavoring agent, a coloring agent, and a preservative.

6. The Chinese herbal medical composition according to claim 1, wherein the Chinese herbal medicine is Kakkon-to, and is present in an amount of 30 w/w % per total amount of the composition.

7. The Chinese herbal medical composition according to claim 1, wherein the Chinese herbal medicine is Kakkon-to, and is present in an amount of 15 w/w % per total amount of the composition.

8. The Chinese herbal medical composition according to claim 2, wherein the Chinese herbal medicine is Kakkon-to, and is present in an amount of 15 w/w % per total amount of the composition.

9. The Chinese herbal medical composition according to claim 6, wherein the base consists of 0.5 w/w % carrageenan, 0.1 w/w % carob bean gum, and 0.2 w/w % xanthan gum, per total amount of the composition, and at least one pharmaceutically acceptable additive selected from the group consisting of a stabilizing agent, a corrective agent, an emulsifying agent, a dispersion agent, a sweetening agent, a flavoring agent, a coloring agent, and a preservative.

10. The Chinese herbal medical composition according to claim 9, wherein the at least one pharmaceutically acceptable additive present in the base are 0.02 w/w % propyl parahydroxybenzoate and 69.18 w/w % water, per total amount of the composition.

11. The Chinese herbal medical composition according to claim 7, wherein the base consists of 1 w/w % carrageenan, 0.25 w/w % carob bean gum, and 0.45 w/w % xanthan gum, per total amount of the composition, and at least one pharmaceutically acceptable additive selected from the group consisting of a stabilizing agent, a corrective agent, an emulsifying agent, a dispersion agent, a sweetening agent, a flavoring agent, a coloring agent, and a preservative.

12. The Chinese herbal medical composition according to claim 11, wherein the at least one pharmaceutically acceptable additive present in the base are at least one sweetening agent, at least one dispersion agent, and at least one preservative.

13. The Chinese herbal medical composition according to claim 12, wherein:

the at least one sweetening agent is selected from the group consisting of glucose, fructose, saccharin sodium, sucrose, D-sorbitol, D-mannitol, and hydrogenated maltose starch syrup, the at least one dispersion agent is selected from the group consisting of glycerin, propylene glycol and water, and the preservative is propyl parahydroxybenzoate.

14. The Chinese herbal medical composition according to claim 11, wherein the at least one pharmaceutically acceptable additive present in the base are 6 w/w % hydrogenated maltose starch syrup, 6 w/w % D-sorbitol, 6 w/w % glycerin, 1 w/w % propylene glycol, 0.02 w/w % propyl parahydroxybenzoate and 64.28 w/w % water, per total amount of the composition.

15. The Chinese herbal medical composition according to claim 2, wherein the at least one pharmaceutically acceptable additive present in the base are at least one sweetening agent, at least one dispersion agent, and at least one preservative.

16. The Chinese herbal medical composition according to claim 15, wherein:

the at least one sweetening agent is selected from the group consisting of glucose, fructose, saccharin sodium, sucrose, D-sorbitol, D-mannitol, and hydrogenated maltose starch syrup, the at least one dispersion agent is selected from the group consisting of glycerin, propylene glycol and water, and the preservative is propyl parahydroxybenzoate.

17. The Chinese herbal medical composition according to claim 7, wherein the at least one pharmaceutically acceptable additive present in the base are at least one sweetening agent, at least one dispersion agent, and at least one preservative.

18. The Chinese herbal medical composition according to claim 17, wherein:

the at least one sweetening agent is selected from the group consisting of glucose, fructose, saccharin sodium, sucrose, D-sorbitol, D-mannitol, and hydrogenated maltose starch syrup, the at least one dispersion agent is selected from the group consisting of glycerin, propylene glycol and water, and the preservative is propyl parahydroxybenzoate.

19. The Chinese herbal medical composition according to claim 1, wherein the sweetening agent is at least one selected from the group consisting of glucose, fructose, saccharin sodium, sucrose, D-sorbitol, D-mannitol, and hydrogenated maltose starch syrup.

* * * * *